United States Patent [19]

Stephan et al.

[11] 4,081,431
[45] Mar. 28, 1978

[54] BLOOD FRACTIONATION

[75] Inventors: Wolfgang Stephan, Dreieichenhain; Ronald Kotitschke, Frankfurt am Main, both of Germany

[73] Assignee: Biotest-Serum-Institut GmbH, Frankfurt am Main Niederrad, Germany

[21] Appl. No.: 639,960

[22] Filed: Dec. 11, 1975

[30] Foreign Application Priority Data

Dec. 14, 1974 Germany .................... 2459291

[51] Int. Cl.$^2$ .............................................. A23T 1/06
[52] U.S. Cl. ................................ 260/112 B; 424/101
[58] Field of Search ..................... 260/112 B; 424/101

[56] References Cited

U.S. PATENT DOCUMENTS

| 3,652,530 | 3/1972 | Johnson et al. | 260/112 B |
| 3,682,881 | 8/1972 | Fekete et al. | 260/112 B |
| 3,869,436 | 3/1975 | Falksveden | 260/112 B |
| 3,916,026 | 10/1975 | Stephan | 424/177 |
| 3,920,625 | 11/1975 | Andersson et al. | 260/112 B |
| 3,973,002 | 8/1976 | Hagan et al. | 260/112 B X |

OTHER PUBLICATIONS

Laursen et al., *Chemical Abstracts*, vol. 67:50,325p (1967).
Reid et al., *Ind. & Eng. Chem.*, vol. 43, No. 5 (1951), pp. 1074–1075.
Tullis et al., *The New England Journal of Medicine*, vol. 273, No. 13 (1965), pp. 667–674.

*Primary Examiner*—Walter C. Danison
*Attorney, Agent, or Firm*—Burgess, Dinklage & Sprung

[57] ABSTRACT

A process for the fractionation of blood comprising passing said blood through a cation exchanger, separating the solids from the plasma, freezing the plasma, thawing the frozen plasma, and separating a first product comprising undissolved cryoprecipitate enriched in factor-VIII protein from plasma fluid. The cryoprecipitate can be concentrated by warm water dissolution and polyethylene glycol precipitation. The plasma fluid, optionally after treatment with β-propiolactone and uv irridiation, is treated with tricalcium phosphate to adsorb factors II, VII, IX and X as a second product. These factors can be eluted with citrate solution. The residual plasma from the initial tricalcium phosphate adsorption is treated with colloidal silica to adsorb impurities and leave a third product which is a storage-stable serum protein solution.

10 Claims, 1 Drawing Figure

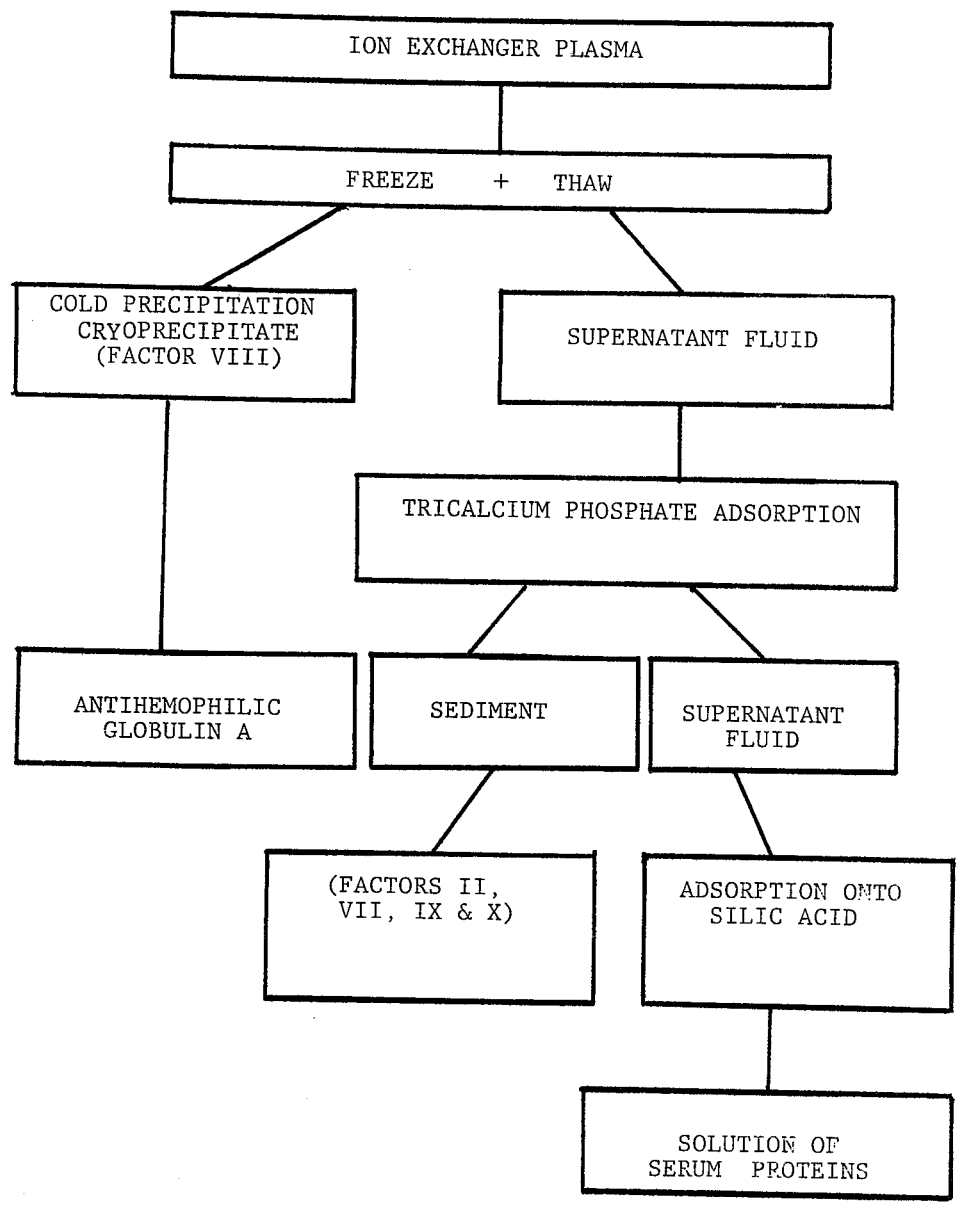

BLOOD FRACTIONATION

BACKGROUND

The invention relates to a method of preparing a prothrombin complex, a solution of serum proteins of good stability in storage, and a concentrate containing antihemophilic globulin A, on the basis of a special starting material.

The great need for human proteins makes it necessary to process human plasma by a method whereby all of the plasma proteins will be obtainable by fractionation with a minimum of loss. The method known as "Cohn fractionation" (Cohn E. J., Gurd F. R. N., Surgenor D. M., Barnes B. A., Brown R. K., Deronaux G., Gillespie J. M., Kahnt F. W., Lever W. F., Lin C. H., Mittelmann D., Monton R. R., Schmid K. and Uroma E.: "A system for the separation of the components of human blood: Quantitative procedure for the separation of the protein components of human plasma" J. Amer. Chem. Soc. 72 (1950), p. 465) is well established, although many plasma proteins are so altered or denatured by this process that they are no longer suitable for administration by infusion, or else they are completely lost. The yields of the desired products, therefore, are very low. Furthermore, the gamma globulin present in the starting material is destroyed.

In the modified Cohn fractionation most frequently used today (Kistler P. and Nitschmann H., "Large Scale Production of Human Plasma Fractions," Vox Sang., 7, (1962), pp. 414–424), only three products are obtained from the plasma, namely albumin, gamma globulin, and coagulable fibrinogen. Due to the danger of hepatitis, the fraction I containing the fibrinogen is made or can be made only from small plasma pools. The alcohol which is used in these fractionations, being an organic solvent, has a denaturing effect on the plasma proteins (Kauzmann W., Avan. Protein Chem., 14 (1959), p 37). The compounds between the hydrophobic protein radicals, which are important to the structure and stability of the proteins, are broken up by the alcohol used in the fractionation, resulting in the denaturation of the proteins and also in the formation of protein aggregations. Such aggregated and denatured proteins are present, for example, in standard gamma globulin preparations unsuitable for intravenous use. Consequently, attempts have been made to isolate proteins without the use of precipitants.

It is known that, after the thawing of citrate plasma at 0° to 8° C after it has been frozen, a small amount of a protein precipitate remains which contains factor VIII activity known as antihemophilic globulin A. The factor VIII content of this fraction is great enough to permit clinically useful factor VIII concentrate to be made from it, the disadvantage, however, being that the blood that is to be processed for cryoprecipitate has to be stabilized with citrate, so that the citrate-containing plasmas then must be processed by the inadequate Cohn method, or else the citrate has to be removed from the plasma by dialysis, which as yet cannot be accomplished on a large technical scale.

Factor IX, together with factors II, VII and X, is part of the so-called "prothrombin complex" or "vitamin K-dependent coagulation factors," all of which are synthesized in the liver. All of the methods for the purification of the prothrombin complex rely on the fact that these factors can be adsorbed onto inorganic adsorbents or onto ion exchange cellulose. In order for the prothrombin complex to be adsorbed directly from plasma onto barium sulfate or calcium phosphate, the blood has to be taken in special anticoagulants, in which case the cell components are no longer usable for transfusion. Barium sulfate yields toxic end products (Tullis J. L., Melin M. and Jurigian P., "Clinical use of human prothrombin complexes," New England Journal of Medicine 273 (1965), 667), and therefore cannot be used.

A method is also known in which a prothrombin complex concentrate can be prepared from plasmas stabilized with citrate, from which the cryoprecipitate has already been removed. This process, nevertheless, has two decided disadvantages:

1. The process is unsuitable for large amounts of plasma. Only small plasma pools can be processed, since the citrate has to be removed by dialysis so that the prothrombin complex will be susceptible of adsorption and elution.
2. The aluminum hydroxide that is used can, in the presence of citrate, result in increased concentration of aluminum due to chelation.

Lastly, a method has also been described for obtaining the prothrombin complex from ACD plasma (citric aciddextrose plasma) by the use of diethylaminoethyl cellulose. In this procedure, however, the plasma must be diluted with an equal volume of water for the purpose of diluting the citrate concentrations prior to adsorption. This creates considerable difficulty in the further fractionation. Consequently, appreciable disadvantages encumber all of the known methods for the production of the prothrombin complex.

The limited usefulness of blood stabilized with anticoagulants appears also in the production of cryoprecipitate. Since in the production of Factor VIII it is desirable to process all possible plasmaphoresis plasmas to yield cryoprecipitate, it has been virtually obligatory to use citrate as the stabilizer.

THE INVENTION

It has surprisingly been found that, setting out from a special starting material, it is possible, without the use of alcohol as in Cohn fractionation, to obtain, side by side, a concentrate of coagulation factors II, VII, IX and X offering no risk of hepatitis, stable serum proteins of good storage life which also present no risk of hepatitis, and a therapeutically useful cryoprecipitate containing factor VIII.

The subject matter of the invention is a method of preparing a solution of stable serum proteins of good storage life, a concentrate containing antihemophilic globulin A, and a prothrombin complex containing prothrombin, proconvertin, Stuart-Prower factor and antihemophilic globulin B, this method being characterized in that the starting material is an ion exchanger plasma which is frozen and thawed again, the supernatant plasma fluid is separated from the protein precipitate containing factor VIII, and the cryoprecipitate obtained is processed in a known manner to produce a factor VIII concentrate, while the plasma fluid is freed of factors II, VII, IX and X by adsorption onto calcium phosphate, and then the coagulation factors and other unstable proteins remaining in the plasma are adsorbed from the plasma fluid onto colloidal silica, and a solution of serum proteins which are stable in storage remains. In the treatment with the colloidal silica, which preferably has a specific surface area of about 50 to 400 m²g, the coagulation factors and other unstable proteins still present in the plasma are removed.

The ion exchanger plasma used is preferably to be not older than about 48 hours. It is advantageously frozen at about −40° C and thawed at temperatures of about 2° to 8° C. After thawing, a protein precipitate is obtained which is insoluble at low temperatures and rich in factor VIII, and which is referred to as a cryoprecipitate by analogy to the cryoprecipitate prepared from plasma stabilized with citrate. The plasma freed from the cryoprecipitate still contains all the factors of the prothrombin complex. The supernatant fluid remaining can be adsorbed with calcium phosphate, thereby removing the factors of prothrombin complex. After treatment with the colloidal silica, a stabilizer-free product forms without any spontaneous coagulation. This process in which therapeutically useful coagulation drugs and human serum are obtained, has the following advantages over processing of plasma by known methods:

1. No stabilizing additives are needed.
2. The erythrocytes can be prepared for infusion simply by suspending them in saline solution.
3. A cryoprecipitate is obtained such as is otherwise obtainable only from citrate-stabilized plasma.
4. The prothrombin complex can be adsorbed onto commonly used inorganic adsorbents and onto sugar and cellulose ion exchangers of high molecular weight.
5. The stabilizer-free "plasma", from which the cryoprecipitate and prothrombin complex have been removed, is virtually of the same composition as a serum. By another adsorption whereby the lipids are also removed, a solution of stable proteins of good storage life is obtained having the following approximate composition:

TABLE

| Fraction | Albumin | $\alpha_1$ | $\alpha_2$ | $\beta$ | $\gamma$-globulin |
|---|---|---|---|---|---|
| Wt. % | 64 | 4 | 8 | 8 | 16 |

The process is further illustrated in the accompanying drawing which is a flow sheet of the process steps and products obtained.

EXAMPLES

The invention will be explained with the aid of the following examples.

EXAMPLE 1

Preparation of antihemophilic globulin concentrate (first product of the process)

Venous blood was taken from donors through a polystyrene-sulfonate cation exchanger in the Na+ form. The blood was centrifuged as quickly as possible after it had been taken, and the erythrocytes, after suspension in physiological saline solution, was reinfused into the donors. The plasma was frozen before no more than 48 hours had elapsed, preferably at −40° C.

In the further processing to be described below, the following reagents were used:
Buffer: 0.02M tri-(hydroxymethyl)-aminomethane (referred to hereinafter as "tris"), adjusted with 1N HCl to a pH of 7.0.
Citrate solution: 0.5M trisodium citrate
Citric acid: 0.02M citric acid solution.
Buffered washing water: 0.02 M tris solution, pH 7.0, containing 8% ethanol.

Factor VIII solution buffer: 5.88 g of trisodium citrate and 2.42 g of tris in one liter of distilled water. The pH 7.0 was adjusted with 19.0 ml of 1N HCl. In addition, one liter of 0.45% sodium chloride solution was added. 15 g of glycine was added per liter of the 1:1 mixture of the two solutions. The pH of the total mixture varies between 6.8 and 7.0.

Procedure:

The frozen plasma was thawed at a temperature under +4° C. It was centrifuged, preferably continuously, or else by individual vessel centrifugation. The cold-precipitation product (cryoprecipitate) served in the further fractionation for the production of a factor VIII concentrate, and the remaining plasma was used for the production of the prothrombin complex concentrate and of the solution of stable serum proteins.

The cryoprecipitate was dissolved in the warm (room temperature, not over 30° C) with tris buffer. Then the solution was cleared by centrifugation and/or filtration of undissolved protein components. The dissolved cryoprecipitate was stirred at room temperature with Al-(OH)₃ gel. After the removal of the adsorbent, the remaining liquid was treated by the addition of 0.5 M trisodium citrate solution (the sodium citrate can also be added in solid form or in other concentrations) to make it an 0.02 M trisodium citrate solution, and adjusted to a pH of 6.1 with 0.02 M citric acid (the citric acid can also be added in solid form or in other concentrations, the pH of 6.1 being the optimum value, although it can be higher or lower, so that the result is a pH range from 5.7 to 7.8). Then polyethylene glycol having an average molecular weight of 4000 was added in solid form to the solution in such an amount that its concentration amounted to a maximum of 5%, and preferably to 3%. After the centrifugation that followed, the sediment was discarded. Colloidal silica was added to the supernatant liquid up to a concentration not greater than 5% and preferably 3% by weight. Especially good results were obtained if the mixture was gently stirred for 2 hours at room temperature. Then it was centrifuged. By increasing the concentration of the polyethylene glycol in the supernatant fluid to no more than 12%, and preferably 10%, the antihemophilic globulin A was precipitated and then removed by centrifugation.

The precipitate was washed with cold (e.g., 2° C) buffered washing water, the washing buffer was then decanted, and the sediment was dissolved by gentle stirring in a small amount of factor VIII solution buffer medium, amounting, for example, to 1/100 of the initial volume of the plasma. The solution was then irradiated with ultraviolet light in a revolving continuous-flow apparatus (Dill apparatus). The radiation intensity amounted to a maximum of 2 mW per minute per square centimeter at a wavelength of 254 nm, and preferably to 1 mW per minute. The irradiated solution was sterilefiltered in a known manner. The protein solution thus obtained contains an antihemophilic globulin concentrate of high effectiveness, and can be freeze-dried without loss of activity. If it is dissolved in half of the decanted volume with water, it contains ten to twenty times the factor VIII activity of a normal plasma, in a protein concentration containing only a twentieth of the amount of protein contained in plasma of the same content of antihemophilic globulin activity. The concentrate can be administered intravenously to patients suffering from a deficiency of factor VIII activity (hemophilia).

Preparation of the prothrombin complex (second product of the process)

The prothrombin complex, also referred to as PPSB, contains the following:

P = prothrombin factor (factor II)
P = proconvertin (factor VII)
S = Stuart-Prower factor (factor X), and
B = antihemophilic globulin B (factor IX).

Reagents:

Caustic soda solution: 1N NaOH solution
β-propiolactone: freshly distilled β-propiolactone.
Tricalcium phosphate: The preparations of a number of manufacturers are suitable (Merck, Riedef de Haen and others).
Citrate solution: 0.05 M trisodium citrate solution.
Acetic acid: 2N acetic acid solution.

Procedure:

β-Propiolactone was added at room temperature to ion exchanger plasma from which the cryoprecipitate had been removed by the method described above, until a concentration of 0.05% to a maximum of 0.3%, preferably a concentration of 0.25%, was reached. The mixture was stirred for one hour at room temperature, and during this period the pH value was maintained at levels between 6.5 and 8.0, preferably at 7.2, by the continuous addition of NaOH. After ultraviolet irradiation in a Dill apparatus, the hydrolysis of the β-propiolactone was continued to completion by the continuous addition of NaOH while maintaining the pH constant, until the pH remained constant without the further addition of NaOH. The ion exchanger plasma treated with β-propiolactone and irradiated was then adsorbed with tricalcium phosphate at room temperature to a concentration of 0.8 wt.-%, preferably with at least 0.1 wt.-% thereof. Greater amounts of tricalcium phosphate can be used, or repeated treatment therewith can be performed, but this offers no advantages. Then the mixture was centrifuged and the sediment was further processed to obtain the PPSB concentrate, while the supernatant liquid served as a starting material for the preparation of the third product of the process. The sediment was eluted with a citrate solution, then eluted a second time with fresh citrate solution, and the combined eluates were treated with colloidal silica to a concentration of no more than 3 wt.-%, and preferably of 0.5 wt.-%. After the adsorption and removal of the silica precipitate, the pH of the supernatant fluid was adjusted with acetic acid to 6.8. It was found advantageous then to concentrate the solution in an ultrafiltration apparatus to about one-third to one-fifth of its volume, then subject it to sterile filtration and freeze-drying.

If the freeze-dried PPSB concentrate is dissolved in water, it contains about 25 times the PPSB factor activity of a normal plasma. The concentrate is suitable for the treatment of deficiency diseases such as hemophilia B.

Preparation of the Solution of Stable Proteins (third product of the process)

Ion exchanger plasma treated as in the two process steps described above was adsorbed with colloidal silica to a concentration of 3 wt.-%, centrifuged and filtered sterile. 1 to 5 wt.-% of silica can also be used.

EXAMPLE 2

The procedure of Example 1 was repeated up to the step of dissolving the second polyethylene glycol sediment, except that heparin was added to the factor VIII solvent in order the more easily to achieve a stabilization of the proteins present in the solution and to facilitate the sterile filtration.

It will be appreciated that the instant specification and claims are set forth by way of illustration and not limitation, and that various modifications and changes may be made without departing from the spirit and scope of the present invention.

What is claimed is:

1. A process for the fractionation of blood consisting essentially of sequentially taking blood from a donor, passing said blood through a cation exchanger, separating the solids from the plasma, freezing the plasma, thawing the frozen plasma and separating from the thawed plasma fluid a first product comprising undissolved cryoprecipitate enriched in factor-VIII protein; dissolving the first product, removing impurities from the solution of the first product, precipitating the factor-VIII protein from the solution; after separation of the first product treating the residual thawed plasma fluid with a solid adsorbent thereby to adsorb the factors II, VII, IX and X, and separating a second product comprising solid adsorbent and the adsorbed factors from the residual plasma; and, after separation of the second product, contacting the residual plasma with colloidal silica and separating a third product comprising a storage-stable serum protein solution from the colloidal silica.

2. A process according to claim 1, wherein the plasma is frozen less than about 4 days after the blood is taken from a donor.

3. A process according to claim 1, wherein freezing is effected at about $-40°$ C.

4. A process according to claim 1, wherein thawing is effected at about 2° to 8° C.

5. A process according to claim 1 wherein the solid adsorbent is tricalcium phosphate.

6. A process according to claim 5, wherein the residual thawed plasma fluid is treated with β-propiolactone prior to contact with the tricalcium phosphate.

7. A process according to claim 5 wherein the colloidal silica has a specific surface area of about 50 to 400 $m^2/g$.

8. A process according to claim 7, wherein the plasma is frozen at about $-40°$ C less than about 48 hours after the blood is taken from a donor, thawing is effected at about 2° to 8° C, the first product is dissolved in warm water and impurities therein are removed by adsorption on $Al(OH)_3$ gel, and the plasma fluid separated from the first product is treated with β-propiolactone prior to contact with the tricalcium phosphate.

9. A process according to claim 8, wherein polyethylene glycol is added to the warm water solution of the first product in an amount sufficient to precipitate the factor-VIII protein.

10. Blood fractions produced by the process of claim 1.

* * * * *